US008046240B2

(12) United States Patent  (10) Patent No.: US 8,046,240 B2
Fukatsu et al.  (45) Date of Patent: Oct. 25, 2011

(54) MEDICAL IMAGE DIAGNOSTIC SYSTEM FOR CREATING ORDER INFORMATION

(75) Inventors: Hiroshi Fukatsu, Nagoya (JP); Muneyasu Kazuno, Nasushiobara (JP); Akira Iwasa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 916 days.

(21) Appl. No.: 11/563,106

(22) Filed: Nov. 24, 2006

(65) Prior Publication Data

US 2007/0167713 A1  Jul. 19, 2007

(30) Foreign Application Priority Data

Nov. 25, 2005  (JP) ................. 2005-340990

(51) Int. Cl.
*G06Q 10/00* (2006.01)
(52) U.S. Cl. ..................... 705/2; 703/2; 705/3
(58) Field of Classification Search .................. 705/2, 3, 705/4
See application file for complete search history.

(56) References Cited

U.S. PATENT DOCUMENTS

| 2004/0128164 | A1* | 7/2004 | DeJarnette et al. | 705/2 |
| 2005/0226405 | A1* | 10/2005 | Fukatsu et al. | 380/1 |

FOREIGN PATENT DOCUMENTS

| JP | 2003-135427 | 5/2003 |
| JP | 2003-164442 | 6/2003 |
| JP | 2004-199710 | 7/2004 |
| JP | 2004-305289 | 11/2004 |
| JP | 2005-27978 | 2/2005 |
| JP | 2005-250856 | 9/2005 |
| WO | WO 03001421 | * 11/2003 |

OTHER PUBLICATIONS

Office Action mailed Jan. 28, 2011, in Japanese Patent Application 2005-340990 (with English Translation), 7 pages I.

* cited by examiner

*Primary Examiner* — Robert Morgan
*Assistant Examiner* — Sean K Hunter
(74) *Attorney, Agent, or Firm* — Oblon, Spivak, McClelland, Maier & Neustadt, L.L.P.

(57) ABSTRACT

In issuing an order, a medical image diagnostic system acquires order issuance support information on the basis of a reference report or a reference image, which an order issuer uses as a basis of order creation. The medical image diagnostic system classifies the order issuance support information on the basis of a table and presents the order issuance support information using a predetermined order issuance support screen. For example, the order issuer selects desired conditions from the order issuance support screen presented to perform order issuance based on the reference report or the like.

20 Claims, 8 Drawing Sheets

| APPARATUS TYPE | INFORMATION COLLECTED | | APPLICATION (CORRESPONDING ITEM) |
| --- | --- | --- | --- |
| | COLLECTION SOURCE | INFORMATION NAME | |
| CT | MEDICAL-REPORT PREPARING SYSTEM | PATIENT ID, PATIENT NAME ... | INSPECTION DETAILS |
| CT | MEDICAL-IMAGE STORING APPARATUS | PATIENT HISTORY | HISTORY LIST |
| CT | MEDICAL-IMAGE STORING APPARATUS – IMAGE | KVP (0×18,0060) | MANIPULATION – KVP |
| ⋮ | ⋮ | ⋮ | ⋮ |

REFERENCE REPORT

Patient Information
ID: 20051129
NAME: XXXXX XXXX  SEX: M

Exam Information
Exam Date: 2005/8/20
Modality: CT
Site: ABDOMEN

Findings:
A tumor is seen at the ventral portion of the left kidney.
Metastatic lung tumor in right S5 and left S3 are detected.
......

Impression:
Left renal cell carcinoma with multiple bone, .....

[Make Link]

CREATE AND DROP LINK

ORDER INPUT SCREEN

ID: 20051129 NAME: XXXXX XXXX  SEX: M
Birth: MAY 13 1960

Dept.: Uro Physician Name: XXXX YYY
Purpose: Follow up
Diagnosis: Renal cell cancer post surgery Site
HEAD
NECK
CHEST
UPPER ABDOMEN
LOWER ABDOMEN
UPPER EXTREMITIES
LOWER EXTREMITIES
MISCELLANEOUS Technique
PLAIN
PLAIN + CE
CE
DYNAMIC
3D-CTA
MISCELLANEOUS X-RAY dosage/Year
24.7 mSv > occupational dosage limit
Adding 10 mSv for this study

[CONFIRM]

ORDER ISSUANCE SUPPORT SCREEN

| PHRASE | APPARATUS TYPE | CANDIDATE |
|---|---|---|
| ABDOMEN | CT | 1: UPPER ABDOMEN, PLANE, 2: UPPER ABDOMEN, CE ...... |
| IMAGING | CT | 1: HEAD, CE, 2: NECK, CE ...... |
| ... | ... | ... |

MEDICAL IMAGE DIAGNOSTIC SYSTEM FOR CREATING ORDER INFORMATION

CROSS-REFERENCE TO RELATED APPLICATIONS

This application is based upon and claims the benefit of priority from prior Japanese Patent Application No. 2005-340990, filed Nov. 25, 2005, the entire contents of which are incorporated herein by reference.

BACKGROUND OF THE INVENTION

1. Field of the Invention

The present invention relates to a medical image diagnostic system that has an order issuance support function performed by using a diagnostic reading report.

2. Description of the Related Art

In general, issuance of an order (an inspection request) in a Radiology Information System (RIS) is executed by a physician in charge who acquires information from a Hospital Information System (HIS) and inputs necessary matters while referring to a diagnostic reading report and the like. An engineer or the like who operates a medical image diagnostic apparatus determines a photographing range, photographing conditions, and the like on the basis of contents of the order issued and executes necessary collection of images. A diagnostic reading doctor compares, for example, for the purpose of observation of progresses, acquired images with images and the like acquired in the last inspection and uses the images for preparation of a report on the inspection. In recent years, as disclosed in, for example, JP-A-2003-164442, there is also proposed a system that reads out, in issuing an order for the same region of the same patient, an order used at the time of photographing of images in the past and uses the order for the present issuance of an order.

However, in acquiring medical images using an order issued by the conventional system, for example, there are the following problems.

First, there is little information concerning photographing in contents included in the conventional order. Therefore, it may be difficult for a doctor and an engineer in charge of collection of images to judge under what kinds of conditions image collection should be performed.

Second, in the conventional issuance of an order, many items are selected or inputted by manual operation. Therefore, a wrong order may be issued because of an operation mistake. In such a case, an acquired image is different from an intended image. In particular, in the case of an inspection for observation of progresses, it is desired that an order issued is reproduction of photographing conditions and the like used in the last inspection. However, when the present inspection is not consistent with the last inspection because of an operation mistake or discrepancy in selection of conditions, it is impossible to compare diagnostic reading with that in the last inspection. If re-inspection is performed, a patient is force to be subjected to unnecessary exposure to radiation.

Third, information necessary for photographing is not always included in an order. Therefore, even when an order used at the time of photographing of images in the past is used, information necessary for photographing may not be obtained, making it difficult to judge under what kinds of conditions image collection should be performed.

Under the present circumstances, as measures against these problems, an engineer or the like in charge of photographing refers to a diagnostic reading report (a reference report) or an image (a reference image) forming a basis of creation of the order and, if necessary, obtains confirmation of a physician in charge, who issued the order, to perform photographing and the like while supplementing insufficient information. However, these measures impose heavy burden on the engineers or the like in charge of photographing and deteriorates efficiency of work because certain length of time is required in carrying out the measures.

BRIEF SUMMARY OF THE INVENTION

The invention has been devised in view of the circumstances and it is an object of the invention to provide a medical image diagnostic system that acquires information from a reference report or a reference image itself, which a physician in charge refers to in issuing an order, and establishes an order using the information.

According to an aspect of the present invention, there is provided a medical image diagnostic system including: an image storing unit that stores plural medical images together with information incidental to the respective images; a report storing unit that stores plural reports including at least link information to medical images; a report specifying unit for specifying a desired report from the plural reports; and an order creating unit that acquires data necessary for an order of photographing on the basis of the report specified and information incidental to a medical image linked by link information included in the report specified and creates order information.

According to another aspect of the present invention, there is provided a medical image diagnostic system including: a report specifying unit for specifying a desired report including at least link information to medical images; and an order creating unit that acquires the report specified and information incidental to a medical image linked by link information included in the report specified from an image storing unit, which stores plural medical images together with information incidental to the respective medical images, and a report storing unit, which stores plural reports, and creates order information.

DETAILED DESCRIPTION OF THE INVENTION

A first embodiment and a second embodiment of the invention will be hereinafter explained with reference to the accompanying drawings. In the following explanation, components having substantially identical functions and structures are denoted by identical reference numerals and signs. Repeated explanations are made only when the explanations are necessary.

First Embodiment

Figure 1:
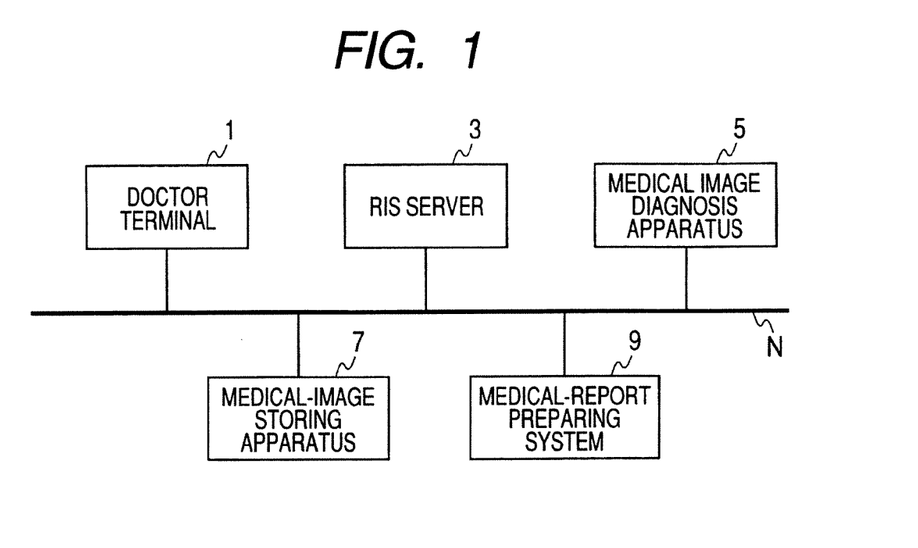
FIG. 1 is a block diagram for explaining a structure of a medical image diagnostic system S according to a first embodiment of the invention.

FIG. 1 is a block diagram for explaining a structure of a medical image diagnostic system S according to the first embodiment. As shown in the figure, the medical image diagnostic system S includes a doctor terminal 1, an RIS server 3, a medical image diagnostic apparatus 5, a medical-image storing apparatus 7, and a medical-report preparing system 9. The respective apparatuses are connected to a network N and capable of exchanging data with one another. Configurations of the respective apparatuses will be explained below.

[Doctor Terminal]

The doctor terminal 1 is a personal computer or a medical work station for displaying a report and an image that a physician in charge or the like observes or presenting an order issuance support screen to the physician in charge. Here, the order issuance support screen is an interface that classifies order issuance support information described later into items corresponding thereto and displays the items in order to facilitate issuance of an order using a reference report or a reference image.

Figure 2:
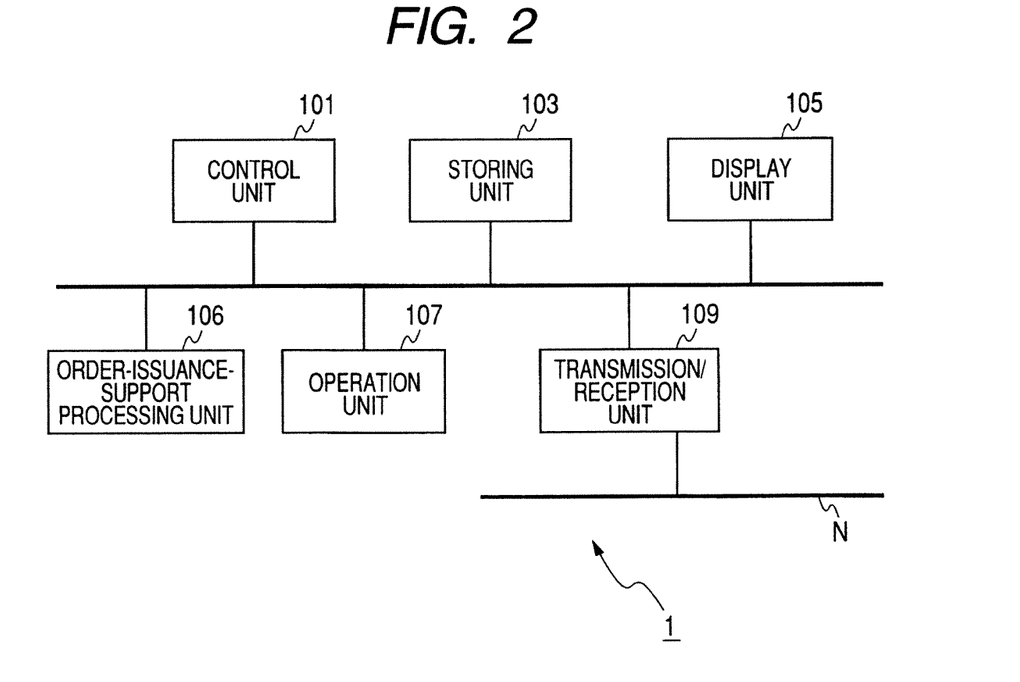
FIG. 2 is a block diagram for explaining a structure of a doctor terminal 1.

FIG. 2 is a block diagram for explaining a structure of the doctor terminal 1. As shown in the figure, the doctor terminal 1 includes a control unit 101, a storing unit 103, a display unit 105, an order-issuance-support processing unit 106, an operation unit 107, and a transmission/reception unit 109.

The control unit 101 collectively controls operations of the doctor terminal 1. In particular, the control unit 101 expands a dedicated program stored in the storing unit 103 on a not-shown memory and controls the display unit 105, the order-issuance-support processing unit 106, the operation unit 107, the transmission/reception unit 109, and the like in accordance with the dedicated program to realize an order issuance support function represented by generation of an order issuance support screen.

The storing unit 103 stores, in addition to various kinds of information such as images and reports, the dedicated program for realizing order issuance support that uses the order issuance support screen.

The display unit 105 displays, in addition to various kinds of information such as medical images and reports, the order issuance support screen generated in accordance with the order issuance support function.

The order-issuance-support processing unit 106 is realized by expanding the dedicated program stored in the storing unit 103 on the not-shown memory. The order-issuance-support processing unit 106 realizes support of issuance of an order by generating the order issuance support screen and presenting the order issuance support screen to an operator via the display unit 105. Further, the order-issuance-support processing unit 106 performs, in response to operation on the order issuance support screen, generation of link information, request for acquisition of order issuance support information, and the like.

The operation unit 107 is an input device that has a mouse, a keyboard, and the like for instructing generation of link information, acquisition of order issuance support information, selection of respective items that should be determined for issuing an order, and the like on the order issuance support screen displayed on the display unit 105.

The transmission/reception unit 109 transmits various kinds of information such as medical images and reports to and receives various kinds of information from other apparatus via network N. In particular, the transmission/reception unit 109 transmits link information, an order issuance instruction, and the like generated in response to predetermined operation on the order issuance support screen to the RIS server 3 via the network N. The transmission/reception unit 109 receives order issuance support information generated in the RIS server 3 via the network N.

[RIS Server]

The RIS server 3 is a server for performing various kinds of information management in a radiology department. The RIS server 3 generates order issuance support information in response to a request for acquisition of order issuance support information from the doctor terminal 1. Here, the order issuance support information is information obtained by editing collectable information on the basis of a reference report or a reference image, which a physician in charge refers to in issuing an order, in order to display the information on the order issuance support screen. The order issuance support information is displayed as contents of the order issuance support screen. The various kinds of information forming the order issuance support information are generated by acquiring information corresponding thereto from the medical-image storing apparatus 7 and the medical-report preparing system 9 on the basis of link information, a reference report, and a reference image received from the doctor terminal 1.

Figure 3:
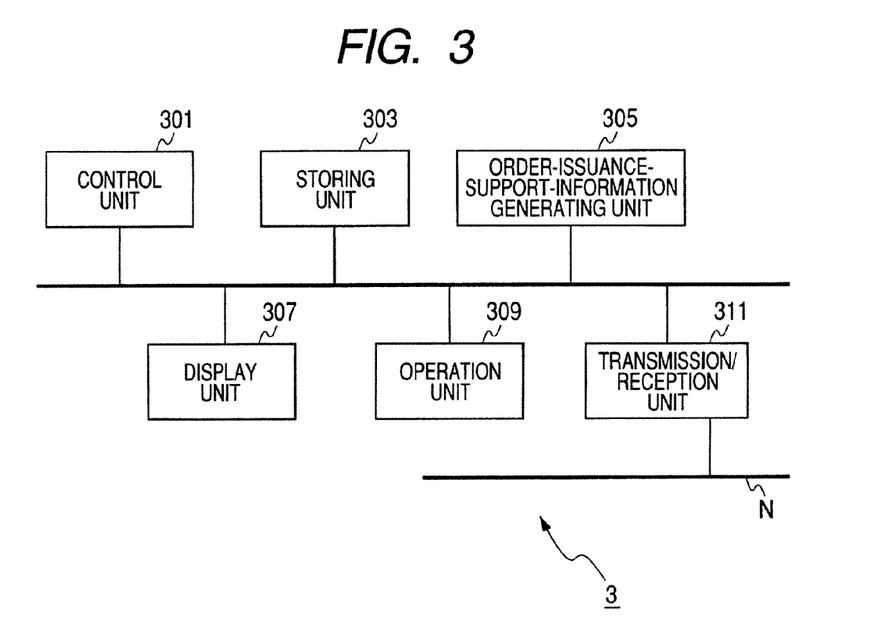
FIG. 3 is a block diagram for explaining a structure of an RIS server 3.

FIG. 3 is a block diagram for explaining a structure of the RIS server 3. As shown in the figure, the RIS server 3 includes a control unit 301, a storing unit 303, an order-issuance-support-information generating unit 305, a display unit 307, an operation unit 309, and a transmission/reception unit 311.

The control unit 301 collectively controls operations of the RIS server 3. The control unit 301 expands a dedicated program stored in the storing unit 303 on the not-shown memory and controls the order-issuance-support-information generating unit 305, the display unit 307, the operation unit 309, the transmission/reception unit 311, and the like in accordance with the dedicated program to realize the order issuance support function represented by generation of order issuance support information.

The storing unit 303 stores, in addition to various kinds of information such as images and reports, the dedicated program for realizing the order issuance support function. The storing unit 303 stores a first correspondence table in which respective kinds of information related to a reference report or a reference image referred to in issuing an order (e.g., patient information, an inspection history, a purposes of an inspection, photographing conditions at the time of image collection, a positioning image, a photographing range, a position of a photographed cross section, a key image, a positions of the key image, and image generation conditions in post processing) and items on the order issuance support screen are associated with each other. It is possible to classify the respective kinds of information forming the order issuance support information into items corresponding thereto on the order issuance support screen by using the first correspondence table.

Figure 4:
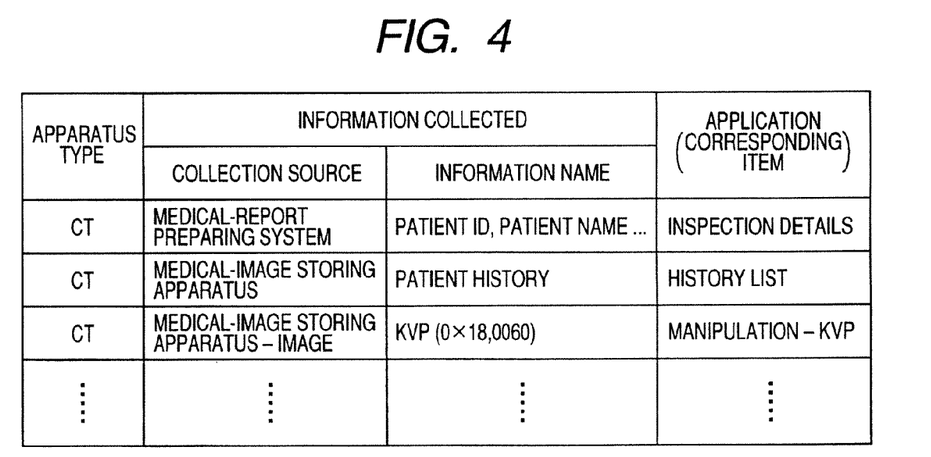
FIG. 4 is a diagram showing an example of a first correspondence table.

FIG. 4 is a diagram showing an example of the first correspondence table. As shown in the figure, in the first correspondence table, respective items on the order issuance support screen (applications of various kinds of information such as inspection details, a history list, and manipulation-KVP) or various kinds of information forming order issuance support information (a patient ID, a patient history, photographing conditions, etc.) and sources of collection of the items or the information (a medical-report preparing system, a medical-image storing apparatus, a medical-image storing apparatus—images, etc.) are associated with each other. At the time of generation of the order issuance support information, according to information or an item, a source of collection of the information or the item is judged with reference to the first correspondence table and various kinds of information are acquired from the source of collection. In the correspondence table, the various kinds of information are classified for each type of apparatuses. This is because, usually, information concerning photographing is different in characteristics for each medical image diagnostic apparatus.

The order-issuance-support-information generating unit 305 is realized by expanding the dedicated program stored in the storing unit 303 on the not-shown memory. The order-issuance-support-information generating unit 305 collects, on the basis of link information, a reference report, and a reference image received from the doctor terminal 1, various kinds of information specified by the reference report or the reference image from the medical-image storing apparatus 7 and the medical-report preparing system 9 via the network N. The order-issuance-support-information generating unit 305 edits the various kinds of information collected using the first correspondence table to generate order issuance support information.

The display unit 307 displays various kinds of information and the like of images and the like.

The operation unit 309 is a device that includes a keyboard, various switches, a mouse, and the like and from which it is possible to input an instruction of the operator.

The transmission/reception unit 311 transmits various kinds of information to and receives various kinds of information from the other apparatuses via the network N. In particular, the transmission/reception unit 311 receives the various kinds of information specified by the reference report or the reference image from the medical-image storing apparatus 7 and the medical-report preparing system 9 via the network N.

[Medical Image Diagnostic Apparatus]

The medical image diagnostic apparatus 5 is one of various apparatuses such as an X-ray computer tomographic apparatus, a magnetic resonance imaging apparatus, an X-ray diagnostic apparatus, a nuclear medical diagnostic apparatus, and an ultrasonic diagnostic apparatus that are used in image collection complying with an order issued by a physician in charge. The medical image diagnostic apparatus 5 may be any one of these kinds of apparatuses. However, to make explanations specific, in this embodiment, it is assumed that the medical image diagnostic apparatus 5 is an X-ray computer tomographic apparatus.

[Medical-Image Storing Apparatus]

The medical-image storing apparatus 7 is used when, for example, a doctor prepares a report while diagnostically reading images. The medical-image storing apparatus 7 registers an image collected by the medical image diagnostic apparatus 5 on management information of a database or the like and manages and stores the image. The medical-image storing apparatus 7 transmits the image stored therein to the other apparatuses via the network N. Further, the medical-image storing apparatus 7 generates a diagnostic image directly from the image collected by the medical image diagnostic apparatus 5 or by applying predetermined image processing to the image and displays the diagnostic image.

Figure 5:
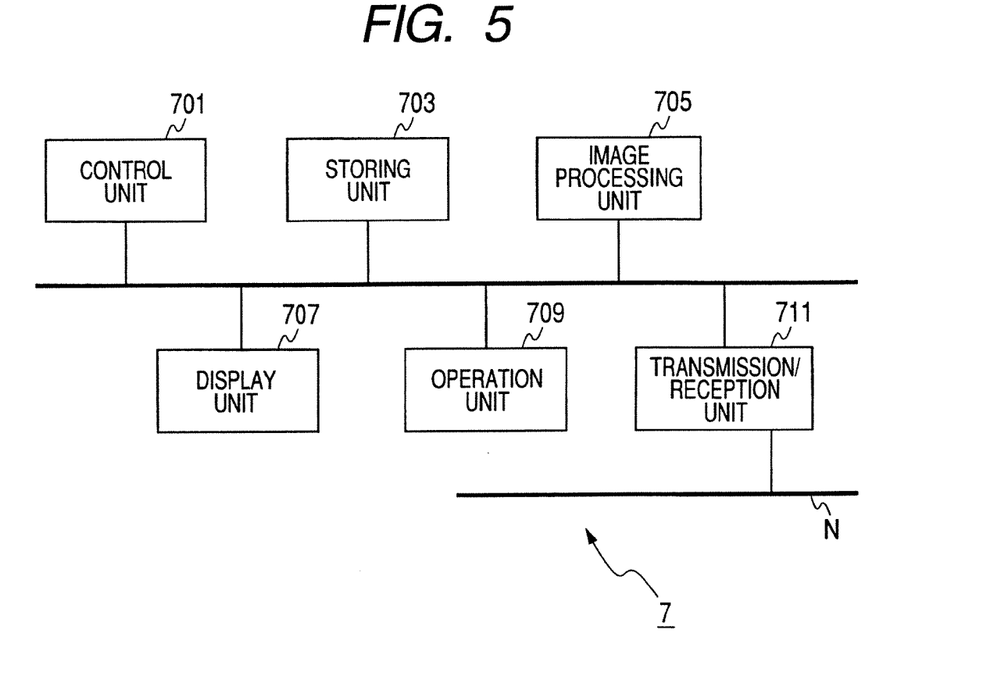
FIG. 5 is a block diagram for explaining a structure of a medical-image storing apparatus 7.

FIG. 5 is a block diagram for explaining a structure of the medical-image storing apparatus 7. As shown in the figure, the medical-image storing apparatus 7 includes a control unit 701, a storing unit 703, an image processing unit 705, a display unit 707, an operation unit 709, and a transmission/reception unit 711.

The control unit 701 collectively controls operations of the medical-image storing apparatus 7. In particular, the control unit 701 retrieves information related to a reference report or a reference image in response to a request from the RIS server 3 and transmits the information to the RIS server 3 via the network N.

The storing unit 703 stores an image acquired by the medical image diagnostic apparatus 5 and information and the like related to the image.

The image processing unit 705 applies predetermined image processing to the image acquired by the medical image diagnostic apparatus 5.

The display unit 707 displays the image and the like acquired by the medical image diagnostic apparatus 5.

The operation unit 709 is a device that includes a keyboard, various switches, a mouse, and the like and from which it is possible to input an instruction of the operator.

The transmission/reception unit 711 receives an information request from the RIS server 3 and transmits the information related to the reference report or the reference image to the RIS server 3 via the network N in accordance with the control by the control unit 701.

[Medical-Report Preparing System]

The medical-report preparing system 9 is an apparatus that prepares a report in which an opinion of a diagnostic reading doctor is recorded in image diagnosis.

Figure 6:
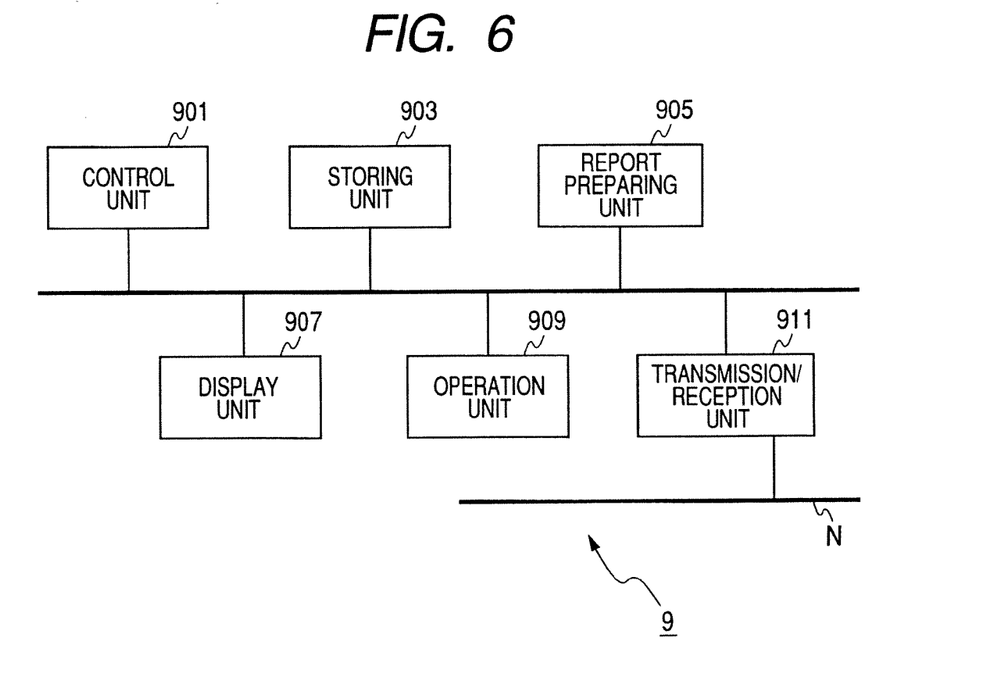
FIG. 6 is a block diagram for explaining a structure of a medical-report preparing system 9.

FIG. 6 is a block diagram for explaining a structure of the medical-report preparing system 9. As shown in the figure, the medical-report preparing system 9 includes a control unit 901, a storing unit 903, an image processing unit 905, a display unit 907, an operation unit 909, and a transmission/reception unit 911.

The control unit 901 collectively controls operations of the medical-report preparing system 9. In particular, the control unit 901 retrieves information related to a reference report, patient information, and the like in response to a request from the RIS server 3 and transmits the information and the like to the RIS server 3 via the network N.

The storing unit 903 stores reports and the like prepared in the past.

The report preparing unit 905 prepares a report in a predetermined format in accordance with an input from the operation unit 909.

The display unit 907 displays an image acquired by the medical image diagnostic apparatus 5, a report preparation screen, a report prepared, information related the foregoing, and the like.

The operation unit 909 is a device that includes a keyboard, various switches, a mouse, and the like and from which it is possible to input an instruction of the operator.

The transmission/reception unit 911 receives an information request from the RIS server 3 and transmits information and the like related to a reference report corresponding to the information request to the RIS server 3 via the network N in accordance with the control by the control unit 901.

Operations

An order issuance operation of the medical image diagnostic system S that has an order issuance support function performed by using a report or the like will be explained. Here, the order issuance support function performed by using a report or the like means a function for acquiring order issuance support information on the basis of a reference report or a reference image, which an order issuer such as a physician in charge uses as a basis of order creation, and presenting the order issuance support information using a predetermined order issuance support screen to improve accuracy concerning the order issuance and reduce work loads. This function is realized mainly by the order-issuance-support processing unit 106 and the order-issuance-support-information generating unit 305.

Figure 7:
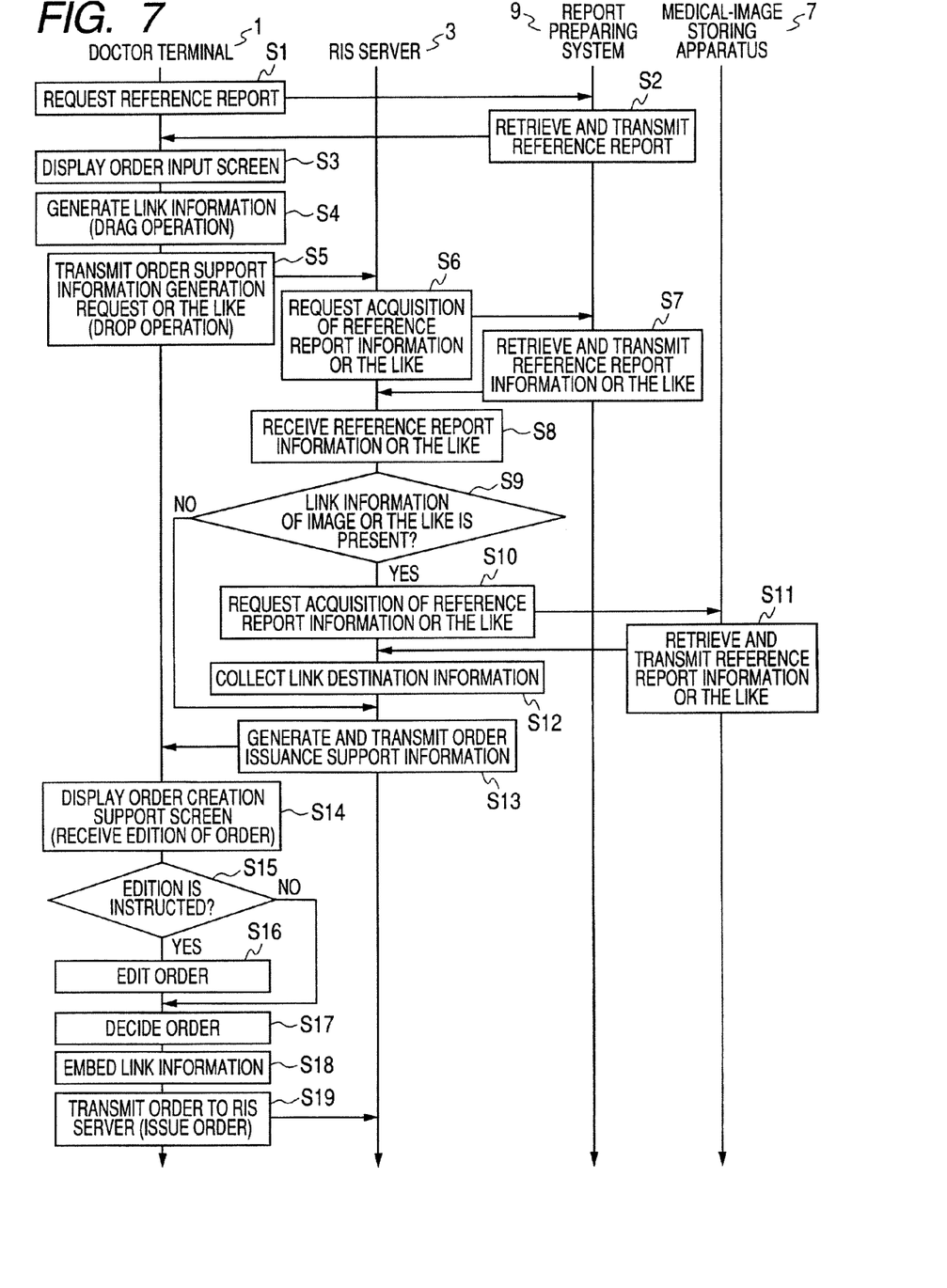
FIG. 7 is a flowchart showing a flow of processing in an order issuance operation of the medical image diagnostic system S.

FIG. 7 is a flowchart showing a flow of processing in the order issuance operation of the medical image diagnostic system S according to the first embodiment. As shown in the figure, first, at an order issuance stage, a reference report request is transmitted from the doctor terminal 1 to the report preparing system 9 in response to predetermined operation by the operator (step S1). In response to the reference report request, the control unit 901 of the report preparing system 9 searches through the storing unit 903, reads out a reference report corresponding to the reference report request, and transmits the reference report to the doctor terminal 1 (step S2).

Figure 8:
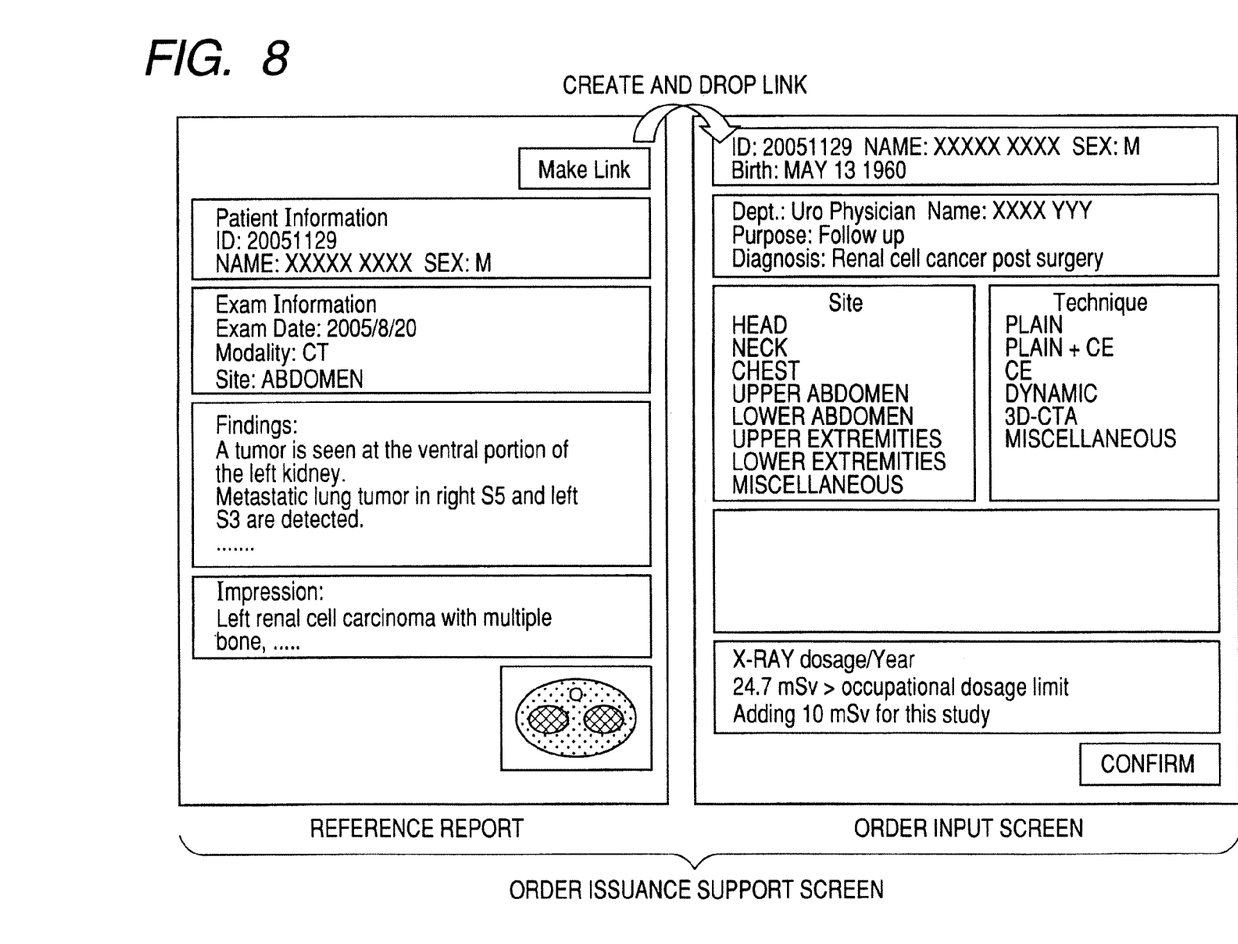
FIG. 8 is a diagram showing an example of an order issuance support screen (before displaying order support information) formed by a reference report display screen and an order input screen.

The order-issuance-support processing unit 106 displays the reference report received as an order issuance support screen together with an order input screen, for example, in a form shown in FIG. 8 (step S3). With this screen, the operator can check contents of the reference report displayed.

If the contents of the report displayed are not desired contents, the medical image diagnostic system repeats the processing from step S1 to S3 to display a desired reference report. The reference report display screen and the order input screen may be started by one application or may be started by individual independent applications.

In response to predetermined operation on the reference report displayed (e.g., predetermined GUI operation such as drag operation on the reference report displayed, designation of a menu item by right click, or click operation of a "Make Link" button shown in FIG. 8), the order-issuance-support processing unit 106 copies link information to the reference report or the like (specific information for specifying a location of a report or an image referred to) (step S4). In response to predetermined operation on the order input screen executed following the operation on the reference report (e.g., drop operation on the order input screen displayed), the order-issuance-support processing unit 106 transmits an instruction for generation of order issuance support information, the link information copied in step S4, and the like to the RIS server 3 via the network N (step S5).

In response to an instruction for generating order issuance support information or the like received from the doctor terminal 1, the order-issuance-support-information generating unit 305 of the RIS server 3 specifies sources of collection of various kinds of information on the basis of the link information and the first correspondence table and transmits requests for acquiring various kinds of information such as information described in a reference report, inspection information related to the reference report, and a key image (an image forming a ground of diagnosis) hyper-linked to the reference report to the report preparing system 9 via the network N (step S6). In response to the request for acquiring various kinds of information, the report preparing system 9 retrieves information corresponding to the request and transmits the information to the RIS server 3 via the network N (step S7). The order-issuance-support-information generating unit 305 receives, via the transmission/reception unit 311, the information described in the reference report or the like transmitted by the report preparing system 9 (step S8).

The order-issuance-support-information generating unit 305 of the RIS server 3 judges whether the reference report received from the report preparing system 9 includes image information linked thereto (step S9). When it is judged that the reference report includes the image information, the order-issuance-support-information generating unit 305 transmits the linked image information and a request for acquiring information incidental to the image to the medical-image storing apparatus 7 on the basis of link information included in the reference report and the first correspondence table (step S10). In response to the request for acquiring the various kinds of information, the medical-image storing apparatus 7 retrieves image information and incidental information corresponding thereto and transmits the image information and the incidental information to the RIS server 3 via the network N (step S11). The control unit 301 receives, via the transmission/reception unit 311, the image information and the like transmitted by the medical-image storing apparatus 7 (step S12).

It is preferable that, when there is no link information to image data related to the reference report, the order-issuance-support-information generating unit 305 instructs the medical-image storing apparatus 7 to directly acquire image data and the like with Q/R (Query/retrieve) or the like using information that can be acquired from contents of the reference report such as a patient ID, a date and time of an inspection corresponding to the reference report, and modality information used.

The order-issuance-support-information generating unit 305 generates information forming order issuance support information from the report related information such as the information described in the reference report, the inspection information, and the image data received. For example, the order-issuance-support-information generating unit 305 generates photographing information at the time of scanning using incidental information of a reference image acquired. In this case, information such as a tube current and a tube voltage of an X-ray generation source in the incidental information and the like only has to be extracted. However, if necessary, predetermined processing (e.g., conversion processing) is applied to the information. The order-issuance-support-information generating unit 305 performs, in accordance with the first correspondence table, edition for, for example, classifying the various kinds of information according to items of an order input screen to generate order issuance support information. The order-issuance-support-information generating unit 305 transmits the order issuance support information generated to the doctor terminal 1 via the network N (step S13).

The order-issuance-support processing unit 105 of the doctor terminal 1 creates an order issuance support screen on the basis of the order issuance support information received from the RIS server 9 and presents the order issuance support screen (displays the order issuance support screen on the display unit 105) (step S14). According to this presentation, an instruction for order edition from the order issuer is received (step S15).

Figure 9:
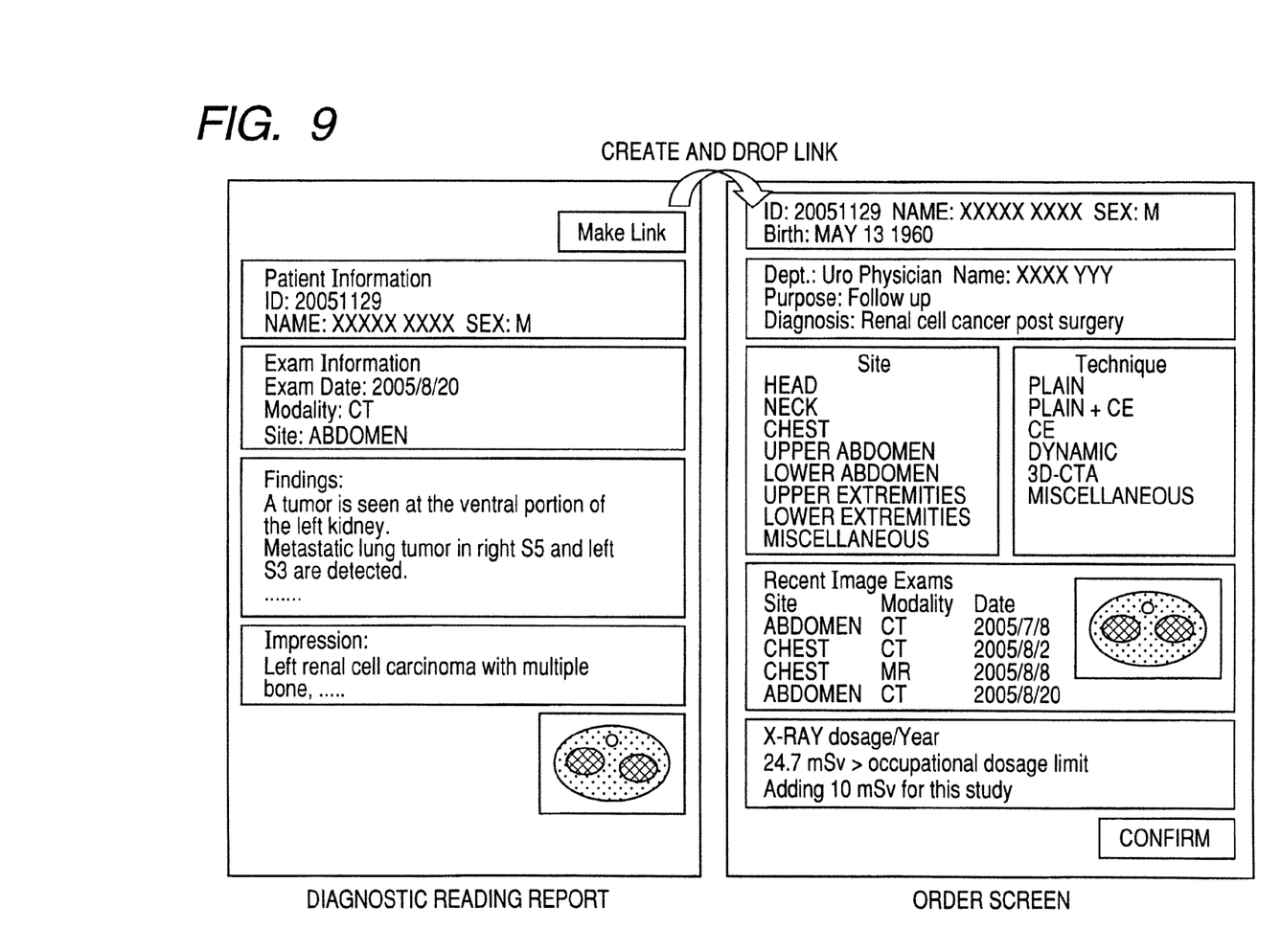
FIG. 9 is a diagram showing an example of the order issuance support screen (after displaying order support information) formed by the reference report display screen and an order input screen.

FIG. 9 shows an example of an order issuance support screen created on the basis of order issuance support information. In the figure, items not included in the order issuance support information are displayed, for example, in a form of reverse display or the like to prevent the items from being selected. When plural pieces of information are classified in one item, these pieces of information are displayed side by side as candidates of the item to cause the order issuer to select the information. The order issuer can visually recognize items related to a reference report or a reference image by observing the screen and edit contents of an order by selecting or changing conditions appropriate for an inspection out of the items.

The order-issuance-support processing unit 105 edits an order in accordance with an instruction inputted via the order issuance support screen (step S16) and decides contents of the order (step S17). The order-issuance-support processing unit 105 embeds link information of the reference report in the order decided (step S18) and transmits the order to the RIS server 3 to perform order issuance (step S19).

Depending on a patient, a type of a report, or the like, plural key images hyper-linked to the reference report may be present. In such a case, at least one desired key image only has to be specified (selected) via the operation unit 309. The order-issuance-support processing unit 106 copies, link information concerning the at least one key image specified in response to drag operation or the like of the mouse. The order-issuance-support processing unit 106 transmits, link information or the like copied in response to drop operation or the like of the mouse, to the RIS server 3 via the network N. Thereafter, it is possible to perform order issuance by executing the processing in steps S6 to S19 described above.

According to the constitution described above, it is possible to obtain the following effects.

According the medical image diagnostic system, in issuing an order, order issuance support information is generated on the basis of description of a reference report or a reference image, which the order issuer uses as a basis of order creation, using hyperlink information or the like and the order issuance support information is presented to the order issuer using the predetermined order issuance support screen. The order issuer can generate an order based on the reference report or the like and issue the order by, for example, selecting desired conditions from the order issuance support screen presented. Therefore, it is possible to issue an order consistent with at least contents of the last inspection (e.g., an order that can reproduce various conditions set in the last inspection at high accuracy) by selecting the last report or the like as a reference report or the like.

According to the medical image diagnostic system, by selecting a reference report or the like to execute predetermined operation (e.g., drag-and-drop of the reference report) and, for example, selecting a desired information out of presented pieces of information, it is possible to issue an order based on a reference report or the like. Therefore, in issuing an order, the order issuer only has to access necessary minimum information. It is possible to reduce work loads on the order issuer.

According to the medical image diagnostic system, in issuing an order, it is possible to create an order based on a reference report or the like simply by selecting desired information out of pieces of information presented by the order issuance support screen. Therefore, it is possible to reduce operation mistakes at the time of order creation, fluctuation in contents of an order by the issuer, and the like and contribute to improvement of a quality of medical practice.

According to the medical image diagnostic system, since an order based on a reference report or the like is created, it is possible to issue an order of detailed contents that can reproduce various conditions set in the last inspect at high accuracy. Therefore, an engineer or the like who performs photographing using a medical image diagnostic apparatus does not have to perform work for, for example, accessing the last report and checking contents of the report by himself/herself at a photographing stage after order issuance. Therefore, it is possible to reduce work loads on the engineer or the like who performs photographing and, as a result, improve inspection efficiency.

According to the medical image diagnostic system, link information of a reference report forming a ground of order issuance is also embedded in an order. Therefore, it is possible to quickly access inspection information forming a ground of an order if necessary by using the link information. This is extremely useful in medium to large-sized hospitals in which majority of inspections are performed for observation of progresses.

Second Embodiment

A second embodiment of the invention will be explained. A medical image diagnostic system S according to this embodiment acquires order issuance support information on the basis of a keyword or a key phrase included in an opinion in a reference report and presents the order issuance support information using a predetermined order issuance support screen to improve accuracy concerning order issuance and reduce work loads.

Figure 10:
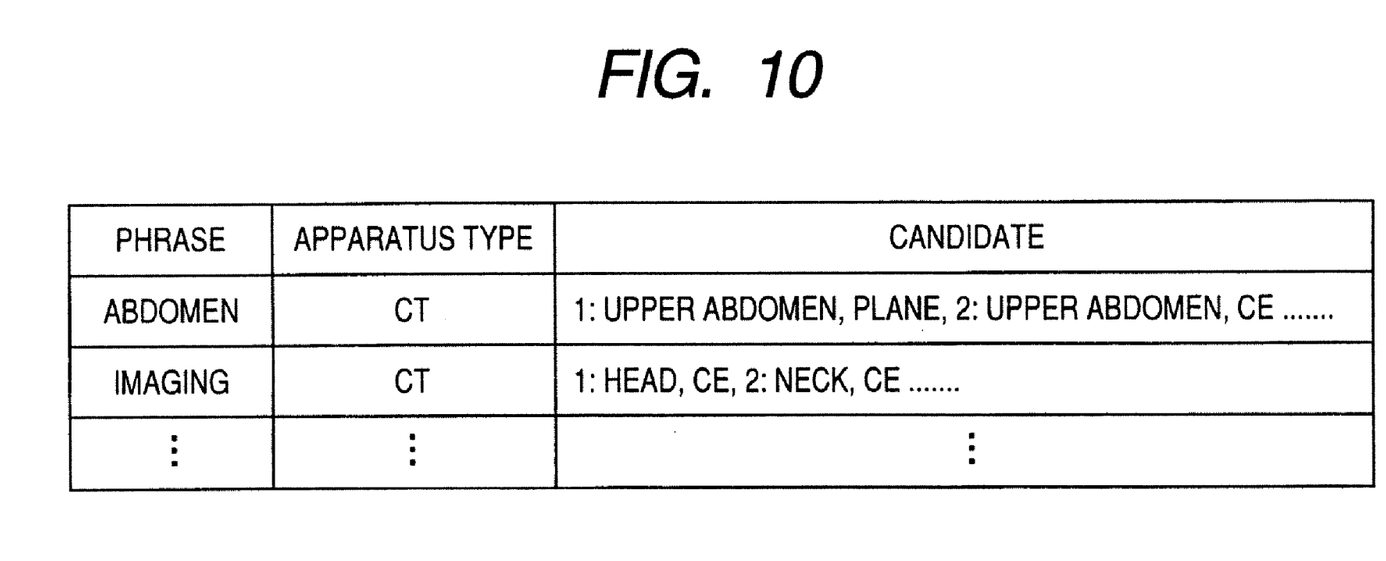
FIG. 10 is a diagram showing an example of a second correspondence table that is referred to when order issuance support information is generated.

FIG. 10 is an example of a second correspondence table referred to when order issuance support information is generated. The second correspondence table is stored in the storing unit 303 of the RIS server 3. As shown in the figure, the second correspondence table associates respective keywords and respective key phrases with various kinds of information such as photographing conditions and indicates information on which modalities the respective keywords and the respective key phrases concern (apparatus type).

The order-issuance-support-information generating unit 305 of the RIS server 3 analyzes a keyword or a key phrase in a reference report received from the doctor terminal 1 and specifies candidate information associated with the keyword or the key phrase with reference to the second correspondence table. The order-issuance-support-information generating unit 305 edits the candidate information specified using the first correspondence table to generate order issuance support information.

Operations

An order issuance operation of the medical image diagnostic system S that has an order issuance support function performed by using a keyword or a key phrase in a report will be explained.

Figure 11:
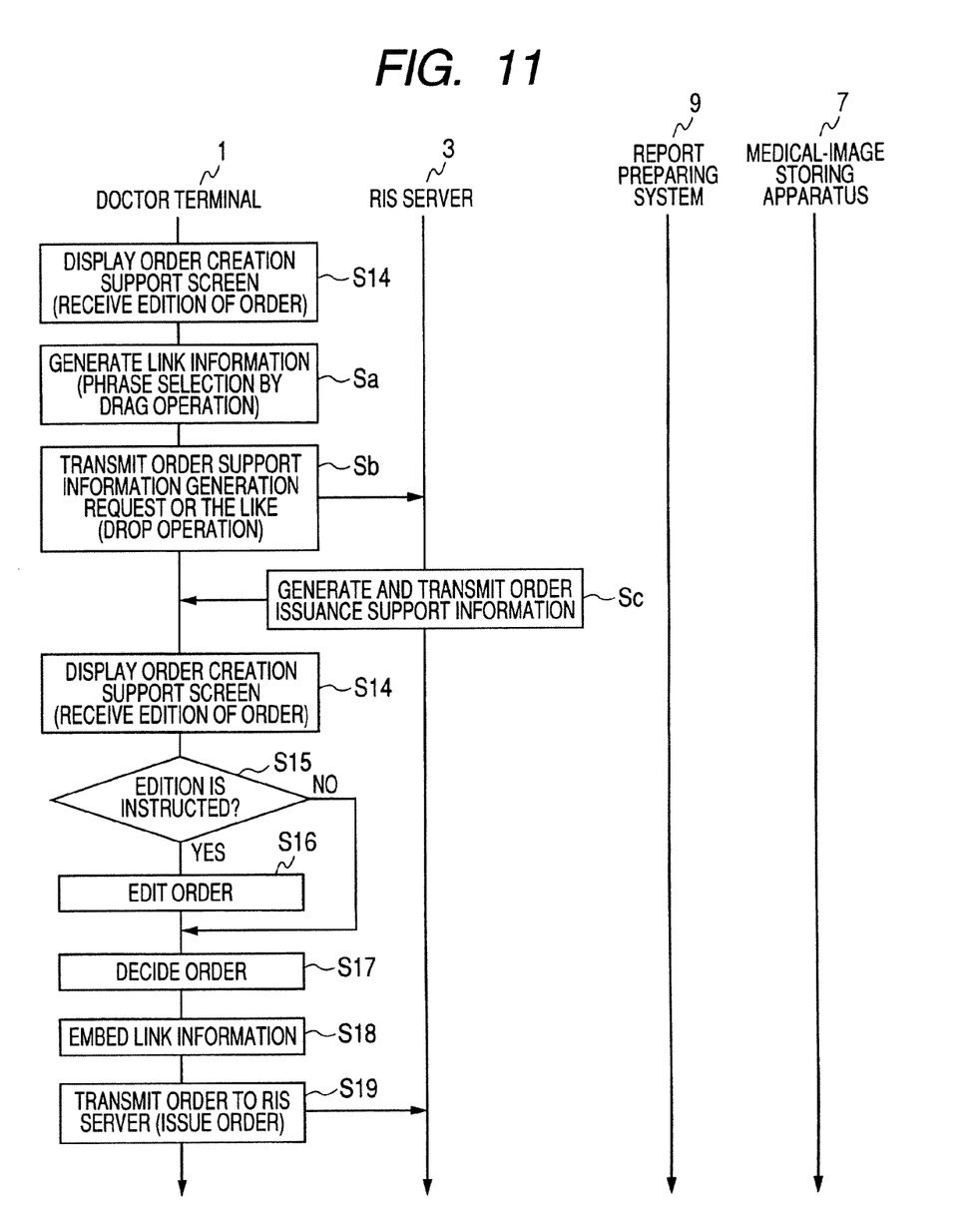
FIG. 11 is a flowchart showing a flow of processing in an order issuance operation of a medical image diagnostic system S according to a second embodiment of the invention.

FIG. 11 is a flowchart showing a flow of processing in the order issuance operation of the medical image diagnostic system S according to the second embodiment. In the figure, processing up to step S14 is the same as that in the first embodiment.

When an order creation support screen is displayed, in response to phrase selection operation on a reference report or an order input screen displayed (e.g., operation for dragging to select a phrase such as "chest" described in the reference report displayed), the order-issuance-support processing unit 106 copies link information in the phrase selected (step Sa). In response to predetermined operation on the order input screen executed following the phrase selection operation (e.g., drop operation on the order input screen displayed), the order-issuance-support processing unit 106 transmits a request for generation of order issuance support information that uses the phrase selected, information on the phrase selected, the link information copied in step Sa, and the like to the RIS server 3 via the network N (step Sb).

The order-issuance-support-information generating unit 305 of the RIS server 3 analyzes a phrase received from the doctor terminal 1 and refers to the second correspondence table stored in the storing unit 303 to extract candidate information associated with the phrase. The order-issuance-support-information generating unit 305 performs edition for, for example, classifying candidate information extracted according to items on the order input screen while referring to the first correspondence table stored in the storing unit 303 to generate order issuance support information. The order-issuance-support-information generating unit 305 transmits the order issuance support information generated to the doctor terminal 1 via the network N (step Sc).

The doctor terminal 1 executes processing from step S14 to step S19 using the order issuance support information received from the RIS server 9.

According to the constitution described above, by selecting a keyword or a key phrase in a reference report and executing predetermined operation (e.g., drag-and-drop of the reference report), it is possible to acquire information linked to the keyword or the like as order issuance support information. The order issuer can issue an order based on the reference report or the like by, for example, selecting desired information out of these pieces of order issuance support information presented. Therefore, in addition to the effects described in the first embodiment, it is possible to realize order issuance with a higher degree of freedom that uses the keyword or the key phrase in the reference report.

The invention is not limited to the embodiments themselves. The elements of the invention may be modified and embodied without departing from the spirit of the invention in an implementation stage. Specific modifications of the invention include the following examples.

(1) It is also possible to realize the respective functions according to the respective embodiments by installing programs for executing the processing for the functions in a computer such as a workstation and expanding the programs on a memory. In this case, a program that can cause the computer to execute the method for the processing may be stored in a recording medium such as a magnetic disk (a floppy (registered trademark) disk, a hard disk, etc.), an optical disk (a CD-ROM, a DVD, etc.) or a semiconductor memory and distributed.

(2) In the respective embodiments, the order-issuance-support processing unit 106 is arranged in the doctor terminal 1 and the order-issuance-support-information generating unit 305 is arranged in the RIS server 3. However, the arrangement of the order-issuance-support processing unit 106 and the order-issuance-support-information generating unit 305 is not limited to this. For example, it is also possible that the RIS server 3 has the order-issuance-support processing unit 106 and the order-issuance-support-information generating unit 305 and executes the processing for generating order issuance support information and the processing for order issuance that uses the order issuance support screen. In such a case, the respective kinds of processing in steps S1 to S5 and steps S14 to S19 in FIG. 7 and steps Sa and Sb in FIG. 11 are executed by the order-issuance-support processing unit 106. The respective kinds of processing in steps S6, S8 to S10, S12, and S13 in FIG. 7 and step sc in FIG. 11 are executed by the order-issuance-support-information generating unit 305. Therefore, all of these kinds of processing are executed in the RIS server 3.

(3) In the medical image diagnostic system according to the respective embodiments, for simplification of explanation, information on a reference report (the entire reference report or contents (a keyword, a key phrase, link information, etc.) of the reference report) is stored in the storing unit 903 of the medical-report preparing system 9 and a key image and the like linked to the reference report is stored in the storing unit 703 of the medical-image storing apparatus 7. However, the storage of the information and the like is not limited to this example. For example, the information on the reference report, the key image linked to the reference report, and the like may be always or temporarily stored in the storing unit 303 of the RIS server 3, may be always or temporarily stored in the storing unit 101 of the doctor terminal 1, may be collectively stored in the storing unit 703 of the medical-image storing apparatus 7, or may be collectively stored in the storing unit 903 of the medical-report preparing system 9. In any case, with operation such as drag-and-drop on a reference report displayed, a key phrase or the like in the report, or a key image linked or hyper-linked to the report on an order issuance support screen as a trigger, it is possible to acquire information corresponding thereto from a storage location specified by link information and generate order issuance support information.

(4) Based on the modifications in (2) and (3) above, it is also possible to constitute the RIS server 3 that has, for example, the order-issuance-support processing unit 106, the order-issuance-support-information generating unit 305, and the storing unit 303 in which information on the reference report, the key information linked to the reference report, and the like are stored. In such a case, it is also possible to constitute the medical image diagnostic system with only the RIS server 3.

It is possible to devise various inventions according to appropriate combinations of the plural components disclosed in the embodiments. For example, several components may be deleted from all the components disclosed in the embodiments. Moreover, the components disclosed in the different embodiments may be appropriately combined.

What is claimed is:
1. A medical image diagnostic system, comprising:
a tangible memory that stores plural medical images together with information incidental to the respective images;
a report storing unit that stores plural reports including at least link information to medical images, each report including findings generated by analysis of the medical images;
a report specifying unit for specifying a desired report from the plural reports; and
an order creating unit that acquires data necessary for creating order information on the basis of the report specified and information incidental to a medical image linked by link information included in the report specified, and creates the order information based on contents of the report specified and based on the information incidental to the medical image linked by the link information included in the report specified, the order information including at least one condition for acquiring an image by performing imaging using a medical image diagnostic apparatus.
2. A medical image diagnostic system according to claim 1, further comprising a link-information specifying unit for specifying, when the report specified includes link information to plural medical images, link information corresponding to at least one of the plural medical images, wherein the order creating unit creates the order information on the basis of the report specified and information incidental to a medical image linked by the link information specified.

3. A medical image diagnostic system according to claim 1, further comprising:
a display unit that displays a support screen for supporting generation of the order information; and
an input unit configured to receive an instruction for creating the order information by applying a predetermined operation to the support screen.

4. A medical image diagnostic system according to claim 3, further comprising a support-information generating unit that generates order generation support information by classifying, on the basis of a first table that associates display items of the support screen with respective kinds of information, information included in the report specified and the information incidental to the medical image linked by the link information included in the report specified, wherein
the display unit displays a support screen including the order generation support information, and
the order creating unit generates the order information on the basis of information selected by the input unit from the order generation support information.

5. A medical image diagnostic system according to claim 4, wherein the support-information generating unit generates the order generation support information in response to a drag-and-drop operation on the support screen performed by using the input unit.

6. A medical image diagnostic system according to claim 1, further comprising a medical-information storing unit that stores medical information corresponding to the plural medical images, wherein
when the report specified includes a predetermined word and link information to medical information related to the predetermined word, the order creating unit generates the order information using the medical information linked by the link information.

7. A medical image diagnostic system according to claim 6, further comprising:
a display unit that displays a support screen for supporting generation of the order information; and
an input unit configured to receive an instruction for creating the order information by applying a predetermined operation to the support screen.

8. A medical image diagnostic system according to claim 7, further comprising a support-information generating unit that generates order generation support information by classifying, on the basis of a first table that associates display items of the support screen with respective kinds of information, information included in the report specified, the information incidental to the medical image linked by the link information included in the report specified, and the medical information linked, wherein
the display unit displays a support screen including the order generation support information, and
the order creating unit generates the order information on the basis of information selected by the input unit from the order generation support information.

9. A medical image diagnostic system according to claim 8, wherein the support-information generating unit generates the order generation support information in response to a drag-and-drop operation on the support screen performed by using the input unit.

10. A medical image diagnostic system according to claim 1, further comprising an order issuing unit that issues an order using the order information generated.

11. A medical image diagnostic system, comprising:
a report specifying unit for specifying a desired report including at least link information to medical images, the report including findings generated by analysis of the medical images; and
an order creating unit that acquires the report specified and information incidental to a medical image linked by link information included in the report specified from an image storing unit, which stores plural medical images together with information incidental to the respective medical images, and a report storing unit, which stores plural reports, and creates order information based on contents of the report specified and based on the information incidental to the medical image linked by the link information included in the report specified, the order information including at least one condition for acquiring an image by performing imaging using a medical image diagnostic apparatus, wherein the order creating unit is implemented as hardware or as a hardware/software combination.

12. A medical image diagnostic system according to claim 11, further comprising a link-information specifying unit for specifying, when the report specified includes link information to plural medical images, link information corresponding to at least one of the plural medical images, wherein
the order creating unit creates the order information on the basis of the report specified and information incidental to a medical image linked by the link information specified.

13. A medical image diagnostic system according to claim 11, further comprising:
a display unit that displays a support screen for supporting generation of the order information; and
an input unit configured to receive an instruction for creating the order information by applying a predetermined operation to the support screen.

14. A medical image diagnostic system according to claim 13, further comprising a support-information generating unit that generates order generation support information by classifying, on the basis of a first table that associates display items of the support screen with respective kinds of information, information included in the report specified and the information incidental to the medical image linked by link the information included in the report specified, wherein
the display unit displays a support screen including the order generation support information, and
the order creating unit generates the order information on the basis of information selected by the input unit from the order generation support information.

15. A medical image diagnostic system according to claim 14, wherein the support-information generating unit generates the order generation support information in response to a drag-and-drop operation on the support screen performed by using the input unit.

16. A medical image diagnostic system according to claim 11, wherein, when the report specified includes a predetermined word and link information to medical information related to the predetermined word, the order creating unit acquires the medical information linked by the link information from a medical information storing unit, which stores medical information corresponding to the plural medical images, and generates the order information.

17. A medical image diagnostic system according to claim 16, further comprising:
a display unit that displays a support screen for supporting generation of the order information; and
an input unit configured to receive an instruction for creating the order information by applying a predetermined operation to the support screen.

18. A medical image diagnostic system according to claim 17, further comprising a support-information generating unit that generates order generation support information by classifying, on the basis of a first table that associates display items of the support screen with respective kinds of information, information included in the report specified, the information incidental to the medical image linked by the link information included in the report specified, and the medical information linked, wherein
the display unit displays a support screen including the order generation support information, and
the order creating unit generates the order information on the basis of information selected by the input unit from the order generation support information.

19. A medical image diagnostic system according to claim 18, further comprising an operation unit for applying a drag-and-drop operation to a screen on which the report specified is displayed, wherein
the support-information generating unit generates the order generation support information in response to a drag-and-drop operation on the support screen performed by using the input unit.

20. A medical image diagnostic system according to claim 11, further comprising an order issuing unit that issues an order using the order information generated.

* * * * *